(12) United States Patent
Lauf et al.

(10) Patent No.: US 11,744,620 B2
(45) Date of Patent: Sep. 5, 2023

(54) FACET PLATE FOR IMPLANT EXPULSION PREVENTION

(71) Applicant: Life Spine, Inc., Huntley, IL (US)

(72) Inventors: Garrett D. Lauf, Hampshire, IL (US); Daniel P. Predick, Wheat Ridge, CO (US); Zeshan Hyder, Munster, IN (US)

(73) Assignee: Life Spine, Inc., Huntley, IL (US)

( * ) Notice: Subject to any disclaimer, the term of this patent is extended or adjusted under 35 U.S.C. 154(b) by 315 days.

(21) Appl. No.: 17/103,053

(22) Filed: Nov. 24, 2020

(65) Prior Publication Data

US 2021/0077156 A1  Mar. 18, 2021

Related U.S. Application Data

(62) Division of application No. 16/171,331, filed on Oct. 25, 2018, now Pat. No. 10,932,823.

(60) Provisional application No. 62/576,846, filed on Oct. 25, 2017.

(51) Int. Cl.
| | |
|---|---|
| A61B 17/70 | (2006.01) |
| A61B 17/88 | (2006.01) |
| A61B 17/86 | (2006.01) |
| A61B 17/56 | (2006.01) |
| A61B 17/80 | (2006.01) |

(52) U.S. Cl.
CPC ...... *A61B 17/7059* (2013.01); *A61B 17/7064* (2013.01); *A61B 17/863* (2013.01); *A61B 17/8897* (2013.01); *A61B 17/808* (2013.01); *A61B 2017/564* (2013.01)

(58) Field of Classification Search
CPC ............ A61B 17/7059; A61B 17/7064; A61B 17/683; A61B 17/8897; A61B 17/808; A61B 2017/564
USPC ......... 606/247, 280, 281, 286, 297, 308, 99, 606/104, 86 B
See application file for complete search history.

(56) References Cited

U.S. PATENT DOCUMENTS

| | | | |
|---|---|---|---|
| 5,662,655 A | 9/1997 | Laboureau et al. | |
| 5,968,046 A * | 10/1999 | Castleman | A61B 17/8625 606/286 |
| 9,987,145 B2 | 6/2018 | Williams | |
| 10,492,841 B2 | 12/2019 | Hartdegen et al. | |
| 2002/0128654 A1 | 9/2002 | Steger et al. | |
| 2004/0153078 A1 | 8/2004 | Grinberg | |
| 2007/0093834 A1 | 4/2007 | Stevens et al. | |
| 2007/0162018 A1* | 7/2007 | Jensen | A61B 17/8863 606/326 |
| 2009/0177203 A1 | 7/2009 | Reiley | |

(Continued)

*Primary Examiner* — Eduardo C Robert
*Assistant Examiner* — David C Comstock
(74) *Attorney, Agent, or Firm* — Foley & Lardner LLP (57) ABSTRACT

A plate and an installation tool are provided for preventing a spinal facet joint implant from expulsing from its implant location between a superior and an inferior vertebra. A k-wire is used in cooperation with the plate and installation tool to guide them to the desired location. The plate includes a central threaded bore situated between one or two superior bone screw or bone connection barb bores and one or two inferior bone screw or bone connection barb bores. The installation tool includes a threaded plug at one end for receipt by the plate's central threaded bore for releasably holding the plate during installation. The installation tool has a superior structure and an inferior structure that can be a cannula or tang depending on the plate's form.

14 Claims, 10 Drawing Sheets

(56) References Cited

U.S. PATENT DOCUMENTS

| | | |
|---|---|---|
| 2010/0280555 A1 | 11/2010 | Aflatoon et al. |
| 2011/0224734 A1 | 9/2011 | Schelling |
| 2013/0053894 A1* | 2/2013 | Gamache .......... A61B 17/7062 606/279 |
| 2014/0081269 A1* | 3/2014 | Biedermann .......... A61B 17/80 606/71 |
| 2015/0100126 A1 | 4/2015 | Melkent et al. |
| 2017/0238980 A1 | 8/2017 | Lauf et al. |
| 2018/0008428 A1 | 1/2018 | Larson et al. |

* cited by examiner

FACET PLATE FOR IMPLANT EXPULSION PREVENTION

CROSS-REFERENCE TO RELATED APPLICATIONS

This U.S. non-provisional patent application is a divisional of U.S. non-provisional patent application Ser. No. 16/171,331 filed Oct. 25, 2018 titled "Facet Plate for Implant Expulsion Prevention and Method of Installation," which claims the benefit of and/or priority under 35 U.S.C. § 119(e) to U.S. provisional patent application Ser. No. 62/576,846 filed Oct. 25, 2017 titled "Facet Allograft/Metal Wedge Expulsion Prevention Plate and Method of Installation," the entire contents of each of which are specifically incorporated herein by reference.

FIELD OF THE INVENTION

The present invention relates to orthopedic devices for the spine such as spine implants and their method of installation and, more particularly, to spine implants and their method of installation directed to facet joints of the spine.

BACKGROUND OF THE INVENTION

The spine can be a source of problems for people of any age. People suffer from various disk conditions, vertebral bone disorders, nerve problems and more. One area of the spine that can cause problems is the facet joint. Facet joints of the spine are in almost constant motion, and thus quite commonly simply wear out or become degenerated in many people. When facet joints become worn or torn, the cartilage may become thin or disappear. This can cause a reaction of the bone of the joint underneath—producing overgrowth of bone spurs and an enlargement of the joints. Such a condition can produce considerable back pain on motion. This condition may be referred to as "facet joint disease," "facet joint syndrome" or another name.

Facet joint disorders are some of the most common of all the recurrent, disabling low back and neck problems, and can cause serious symptoms and disability. In unusually severe and persistent problems, degeneration of the adjoining disc is nearly always also present so the spine segment may require a bone fusion surgery to stop problems with both the associated disc and facet joint.

One technique for facet joint fusion surgery is to install an implant in/between the facet joint along with a plate fastened to the upper and lower vertebrae associated with the facet joint for stabilizing and restricting movement of the vertebrae. The implant may or may not have allograft for fusion. A problem with the technique is the tendency for the implant to migrate out of the facet joint. It is therefore one object of many objects of the present invention to address implant migration.

SUMMARY OF THE INVENTION

The present invention is a plate, installation tool and installation accoutrements, and method of installation for preventing allograft and/or implant (e.g. allograft or a wedge such as, but not limited to, a metal or plastic wedge, and hereinafter, "wedge") from expulsing posteriorly from its implant location in a spinal facet joint.

The plate is placed posterior to the wedge with a fastener (e.g. a barb or screw) installed (previously or in-situ) on the plate superior to the wedge and another fastener (e.g. barb or screw) installed (previously or in-situ) on the plate inferior to the wedge. Placement of the plate is critical, which is why a k-wire and an installation tool are used in cooperation with the wedge (implant) in order to guide the plate down to the correct location. Once the k-wire is properly placed, the installation tool with the plate releasably connected to its front is guided by the k-wire to a proper site for attachment of the plate onto the vertebral bodies and over the wedge (implant).

The plate includes a central threaded bore situated between the superior bore and the inferior bore. In one form, the installation tool includes a threaded plug at one end, and/or in another form, the installation tool has a central channel, cannula, tube or the like (between superior and inferior channels, cannulas, tubes, or the like, if any) that allows a threaded plug accoutrement (tool) to extend from its end, in order to threadedly attach the threaded plug to the central threaded bore of the plate for releasably holding the plate during installation.

The installation tool has a superior channel, cannula, tube or the like that allows a driver tool to direct a fastener to a superior bore of the plate for attaching the fastener and thus a superior portion of the plate to superior vertebral bone, and an inferior channel, cannula, tube or the like that allows the driver tool to direct a fastener to an inferior bore of the plate for attaching the fastener and thus an inferior portion of the plate to inferior vertebral bone. Once the plate is fully fastened, the installation tool and k-wire are removed.

In one form, the plate has a superior bore and an inferior bore both lateral to the central threaded bore for utilizing bone screws as fasteners. The plate may have a second or secondary superior bore and a second or secondary inferior bore also both lateral to the central threaded bore for utilizing bone screws as further/second/secondary fasteners. These second/secondary bone screws are likewise installed via the screw driver accoutrement/tool that is inserted through the superior and inferior channels, cannulas, tubes or the like of the installation tool. In another form, the plate has a superior barb and an inferior barb as fasteners previously connected to or as part of the plate and disposed lateral to the central threaded bore. The plate includes a superior bore lateral to the superior barb and an inferior bore lateral to the inferior barb. The superior and inferior bores allow connection to superior and inferior nubs or tangs at the end of the installation tool, the superior nub/tang at the end of the superior channel, cannula, tube or the like and the inferior nub/tang at the end of the inferior channel, cannula, tube or the like.

Further aspects of the present invention will become apparent from consideration of the drawings and the following description of forms of the invention. A person skilled in the art will realize that other forms of the invention are possible and that the details of the invention can be modified in a number of respects without departing from the inventive concept. The following drawings and description are to be regarded as illustrative in nature and not restrictive.

BRIEF DESCRIPTION OF THE DRAWING FIGURES

The features of the invention will be better understood by reference to the accompanying drawings which illustrate forms of the present invention, wherein.

It should be appreciated that dimensions of the components, structures, and features of the present plate and installation tools can be altered as desired.

DETAILED DESCRIPTION OF THE INVENTION

Figure 1:
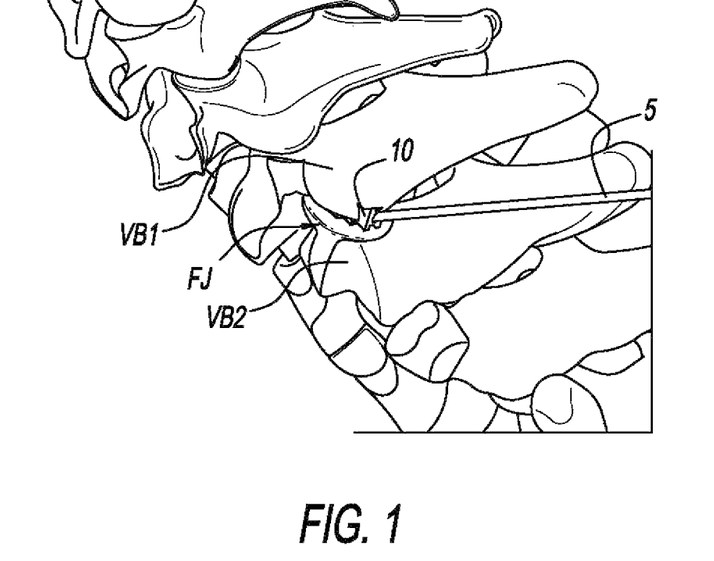
FIG. 1 is a posterior view of a portion of the spine with a wedge installed in a facet joint between two vertebral bodies and a k-wire situated to install a plate.

FIG. 1 shows a portion of a human spine wherein an implant 10, such as, but not limited to, allograft, a wedge of, without being limiting or exhaustive, metal, plastic, and/or ceramic with or without bone fusion material, and/or other type of implant (hereinafter, collectively, "wedge") situated between a facet joint FJ of a superior vertebra VB1 and an inferior vertebra VB2. The wedge 10 has been previously implanted. Also shown in FIG. 1 is a k-wire 5 attached to a posterior pocket (not discerned) of the wedge 10. The k-wire 5 has been previously installed. The vertebrae VB1 and VB2 are ready to receive an implant expulsion prevention plate ("plate" and its variations) fashioned in accordance with the present principles.

Figure 2:
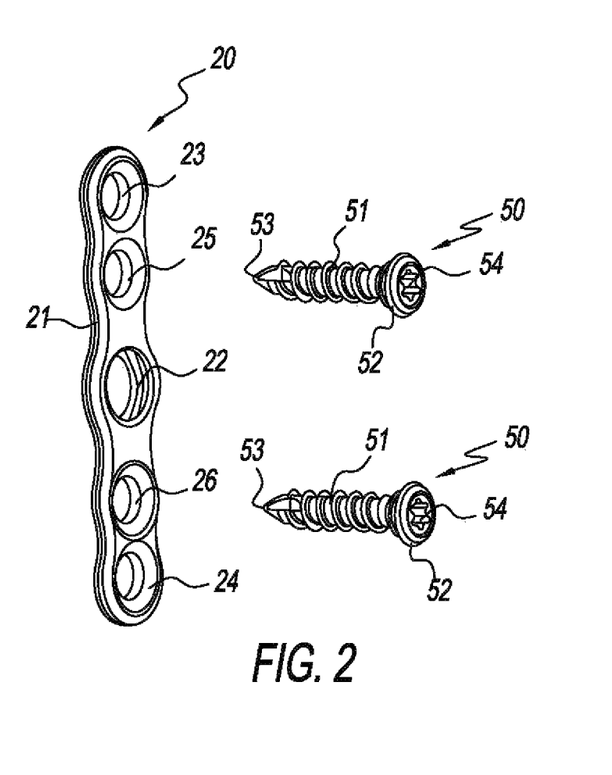
FIG. 2 is an isometric view of one form of an implant expulsion prevention plate for a spinal facet joint implant fashioned in accordance with the present principles with bone screws shown exploded relative to the plate.
Figure 3:
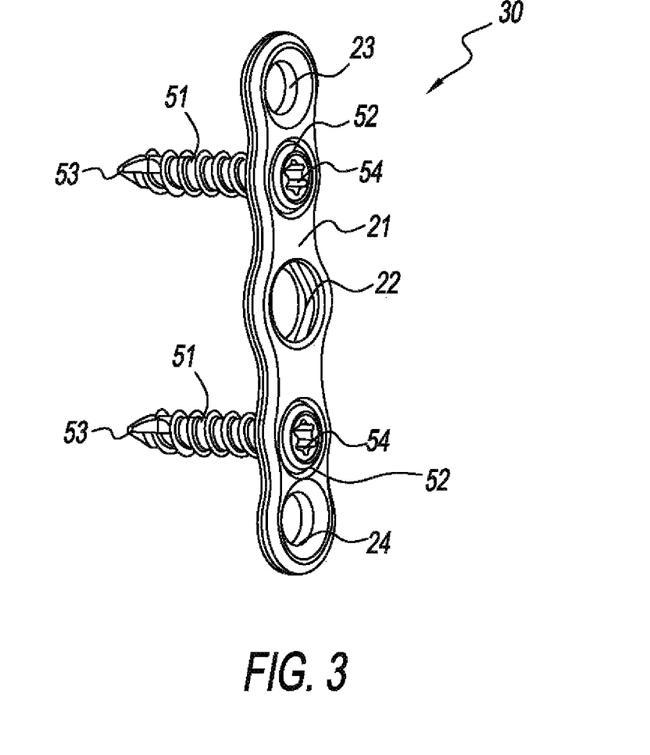
FIG. 3 is an isometric view of the present implant expulsion prevention plate of FIG. 1 with bone screws installed.
Figure 4:
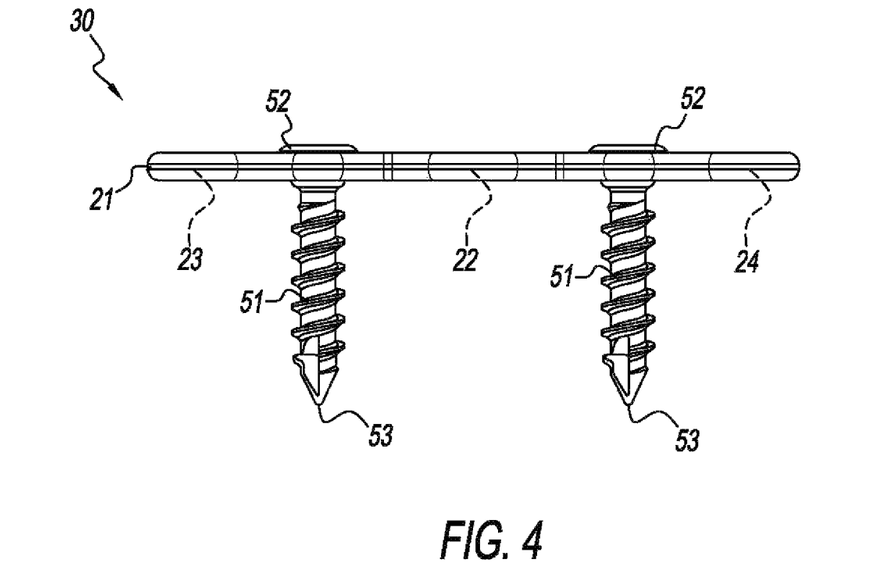
FIG. 4 is a side view of the present implant expulsion prevention plate of FIG. 3.

FIGS. 2-4 show various views of a plate construct 30 fashioned in accordance with the principles of the present invention, the plate construct 30 comprising a plate 20 and bone screws 50. The plate construct 30 is used to aid in preventing expulsion of the wedge 10 (or other implant or otherwise) from the facet joint FJ. The bone screws 50 are used to fasten, attach, fix, connect or otherwise affix the plate 20 to the superior and inferior vertebrae VB1, VB2.

A bone screw 50 is fashioned from a known bio-compatible material and is characterized by an externally threaded shaft or shank 51 having a tip 53 at one end of the threaded shaft 51 and a head 52 at another end of the shaft 51. The head 52 has a socket 54 having an internal configuration such as, but not limited to, a hexagon, that receives a like configured driver/driving tool (see driver/driver end 56 of driver 55 seen in FIGS. 9 and 10) for installing the bone screws.

The plate 20 is fashioned from a bio-compatible material such as is known in the art, and is defined by a flat, elongated, generally planar body 21. While not shown, the body 21 may have a slight curvature for miming anatomy. The plate 20 has a plurality of bores along its length. In particular, the body 21 has a center, central, or middle threaded bore 22 of a first diameter, a first bone screw bore 25 of a second diameter situated laterally adjacent the central threaded bore 22 on the superior end of the body 21, a second bone screw bore 26 of the second diameter situated laterally adjacent the central threaded bore 22 on the inferior end of the body 21, and optionally a third bone screw bore 23 of the second diameter situated laterally adjacent the first bone screw bore 25 distal the central threaded bore 22, and optionally a fourth bone screw bore 24 of the second diameter situated laterally adjacent the second bone screw bore 26 distal the central threaded bore 22, the nomenclature first, second, third, and fourth being arbitrary. As seen in the other figures, the bone screws 50 are initially used in primary bone screw bores 25, 26 of the body 21 to fasten the plate 20 to the vertebrae VB1, VB2. The secondary bores 23, 24 may or may not be used as desired. The nomenclature primary and secondary being arbitrary.

Figure 5:
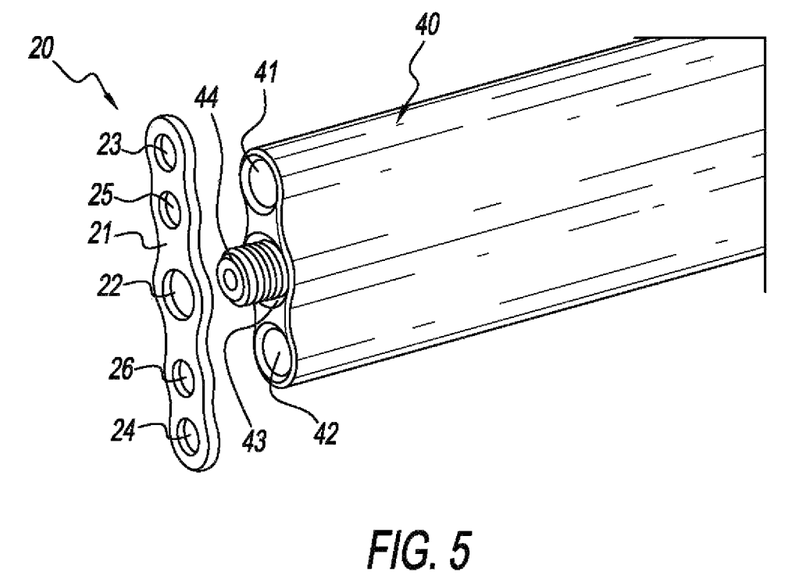
FIG. 5 is an isometric view of an end of an installation instrument for installing the implant expulsion prevention plate of FIGS. 2-4, with the plate shown exploded relative to the end of the installation instrument.
Figure 6:
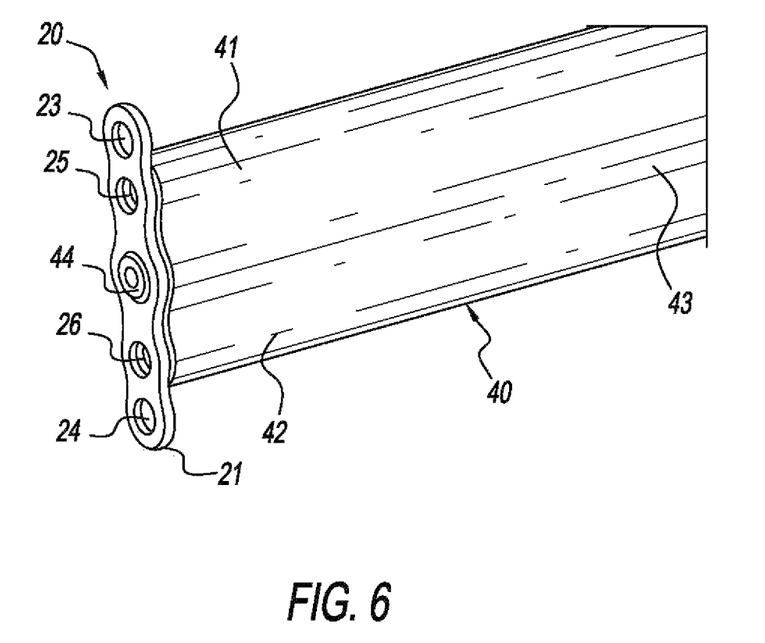
FIG. 6 is an isometric view of the end of the installation instrument of FIG. 5 with the implant expulsion prevention plate attached thereto.
Figure 7:
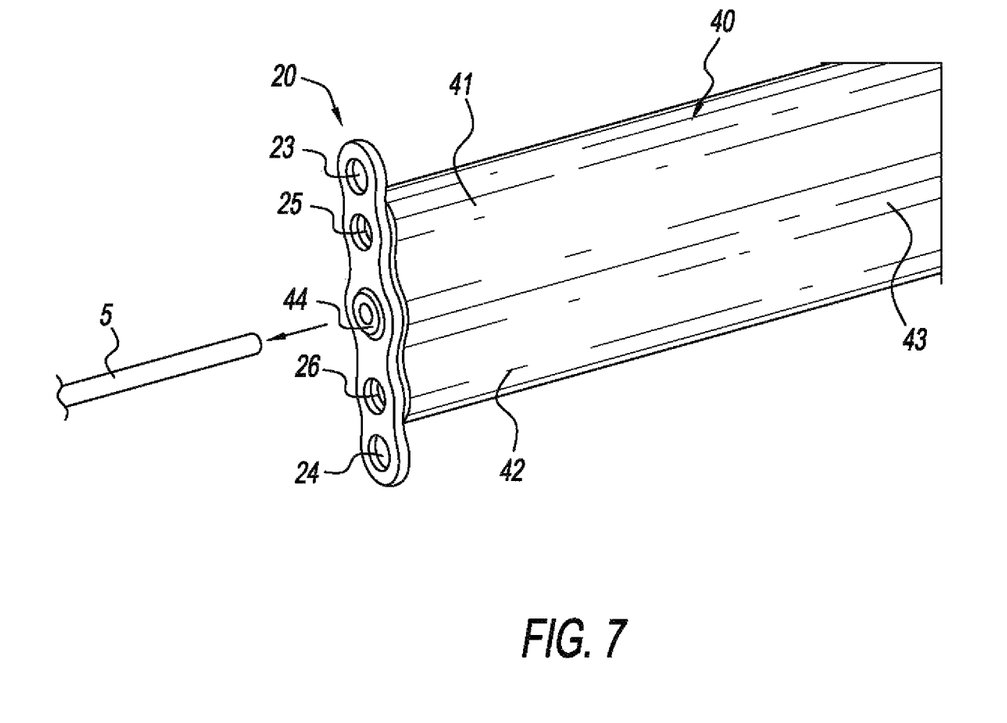
FIG. 7 is an isometric view of the end of the installation instrument of FIG. 6 with the implant expulsion prevention plate attached thereto ready for receipt onto the k-wire.
Figure 8:
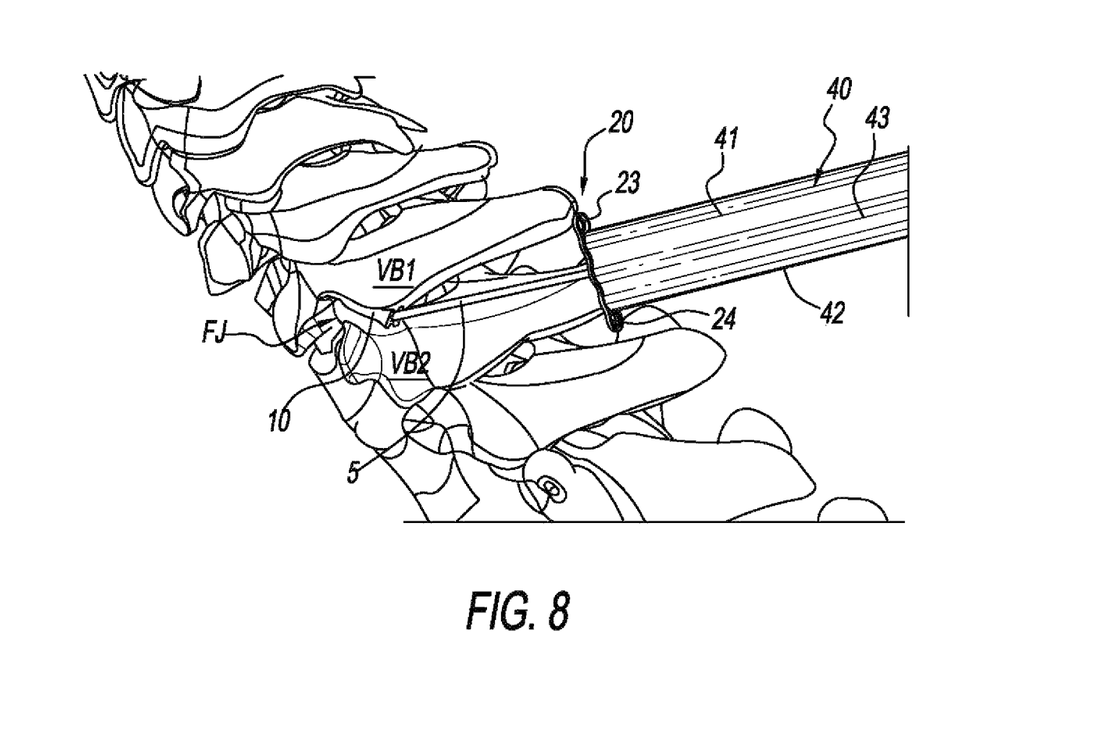
FIG. 8 is a posterior view of a portion of the spine with a wedge (implant) installed in a facet joint between a superior vertebra and an inferior vertebra, with the installation instrument and the connected plate of FIG. 7 being guided down the k-wire.

Installation of the plate 20 is illustrated as herein described. FIG. 5 shows an installation instrument, tool, installer or the like 40 that is made from a typical, bio-compatible surgical instrument material. The installer 40 has a center or central tube, cannula, cylinder, channel or the like 43, an upper or superior tube, cannula, cylinder, channel or the like 41 at a superior side of the central cannula 43, and a lower or inferior tube, cannula, cylinder, channel or the like 42 at an inferior side of the central cannula 43. A threaded plug 44 with a bore therethrough is shown at the end of the central cannula 43, the threaded plug 44 may be permanent to the instrument or may be a separate accoutrement tool to the construct that is received in the central cannula 43 and passed through as necessary. The plate 20 is received onto the installer 40 by threading the threaded central bore 22 of the plate 20 onto the threaded hub 44 of the installer 40. When the plate 20 is so received, as shown in FIG. 6, the upper (superior) primary bone screw bore 25 aligns with the opening of the superior cannula 41 of the installer 40, while the lower (inferior) primary bone screw bore 26 aligns with the opening of the inferior cannula 42 of the installer 40. At this point, the installer 40 is ready to allow placement of the plate 20 onto the vertebrae VB1, VB2 and over the implant 10. As shown in FIG. 7, the installer and plate are received by the k-wire 5. Particularly, the k-wire is received into bore of the threaded hub 44 and into the central cannula 43. As shown in FIG. 8, the plate 20 is guided by the installer 40 into position by the k-wire 5.

Figure 9:
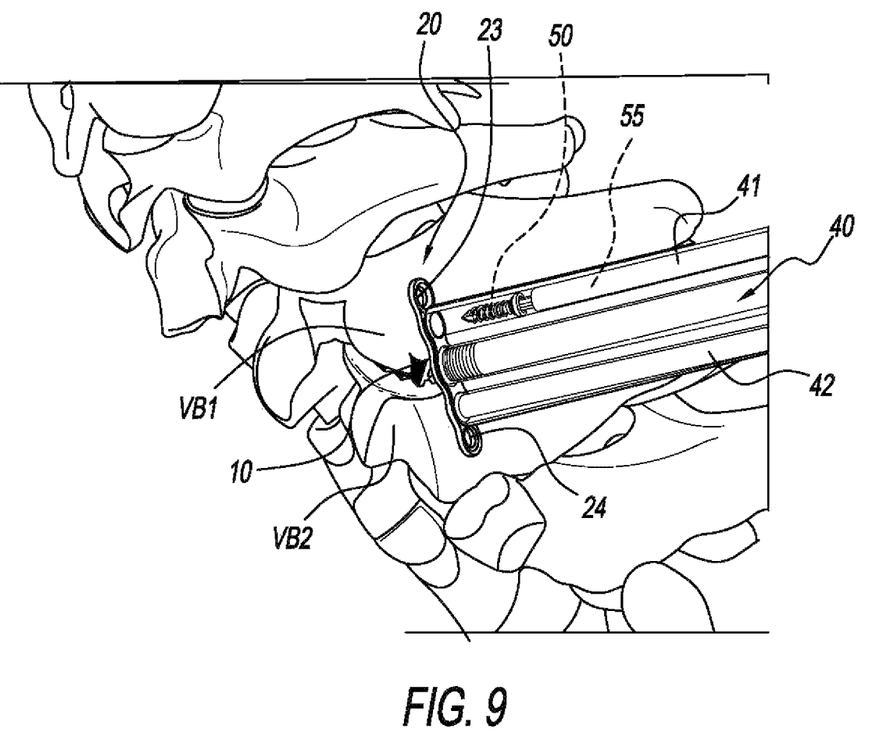
FIG. 9 is the posterior view of the portion of the spine of FIG. 8 with the installation instrument/implant expulsion plate in place to attach the plate to the vertebrae, showing a screw driver tool in the installation instrument and ready to drive a bone screw through the superior bore of the implant expulsion prevention plate and into the vertebra in order to fasten the superior portion of the plate to the vertebra.
Figure 10:
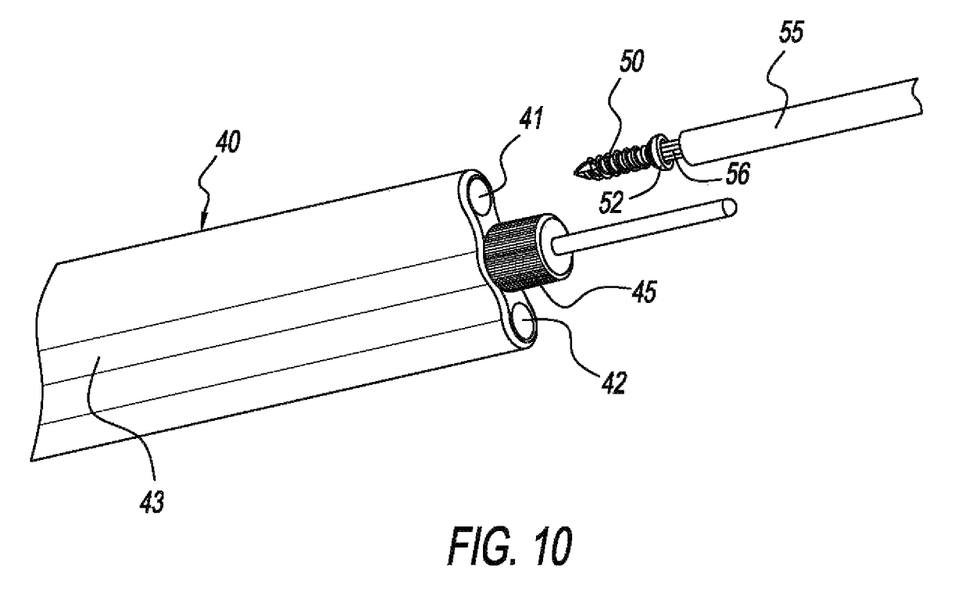
FIG. 10 is an isometric view of the portion of the present installation instrument ready to receive the screw driving tool and a central plug tool.
Figure 11:
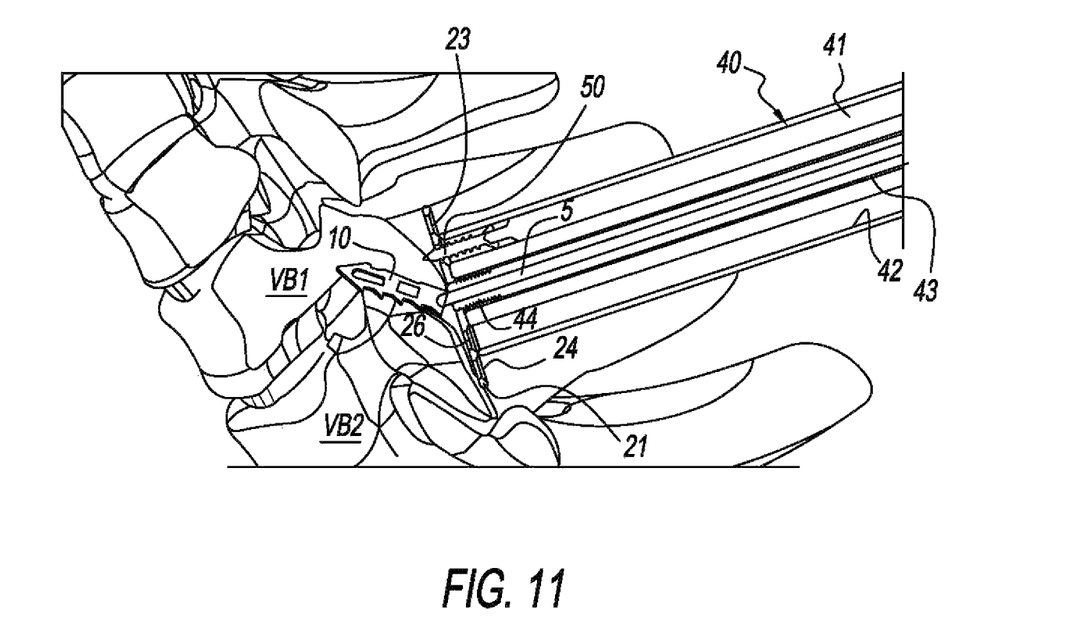
FIG. 11 is the posterior view of the portion of the spine of FIG. 9 illustrating the various components in sectional.
Figure 12:
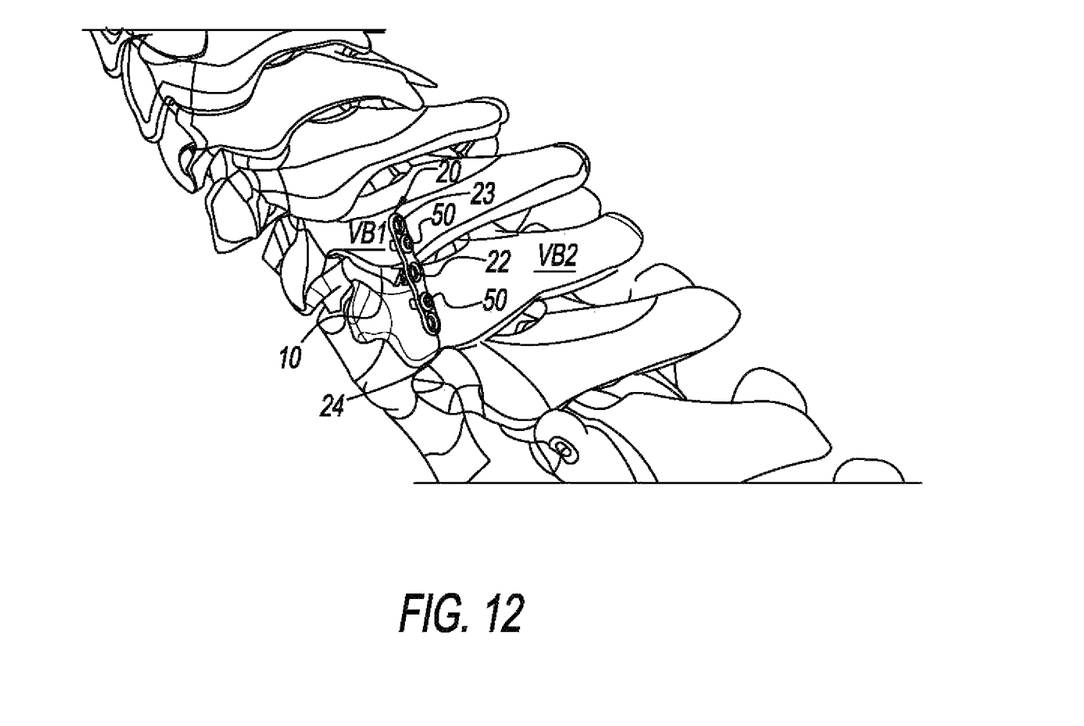
FIG. 12 is the posterior view of the portion of the spine of FIG. 8 with the implant expulsion prevention plate fastened to the vertebrae.

At this point, the plate 20 is ready for attachment to the vertebrae VB1, VB2. As illustrated in FIGS. 9-11, while the plate 20 is held against and over the implant 10, a screw driver/installer 55 with a driving end 56 configured for receipt in the socket 54 of the screw head 52 of the bone screw 50 is received into the superior and inferior cannulas 41, 42 to drive a screw through the primary bone screw bores 25, 26 to attach the plate 20 as shown in FIG. 12. Bone screws 50 may be provided in the secondary bone screw bores 23, 24 if desired.

Figure 13:
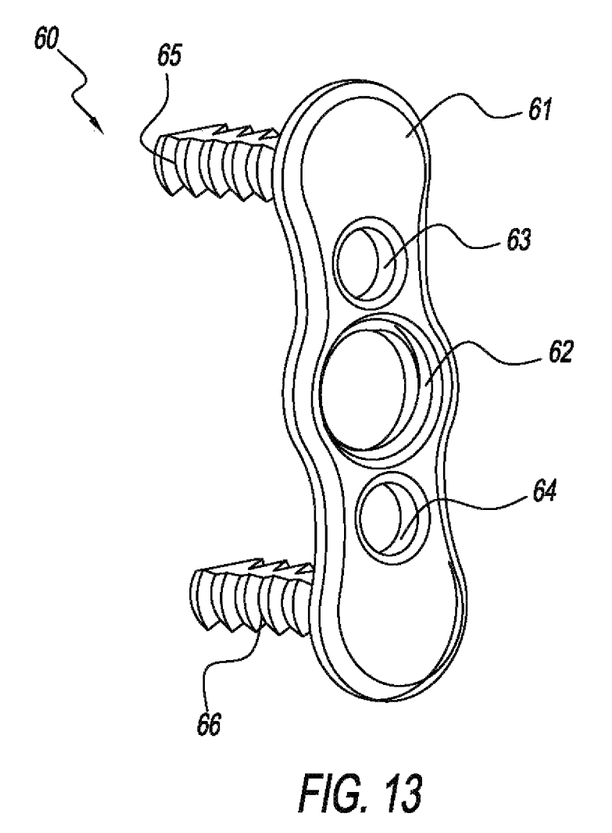
FIG. 13 is an isometric view of another form of an implant expulsion prevention plate for a spinal facet joint implant fashioned in accordance with the present principles with integral connection barbs.
Figure 14:
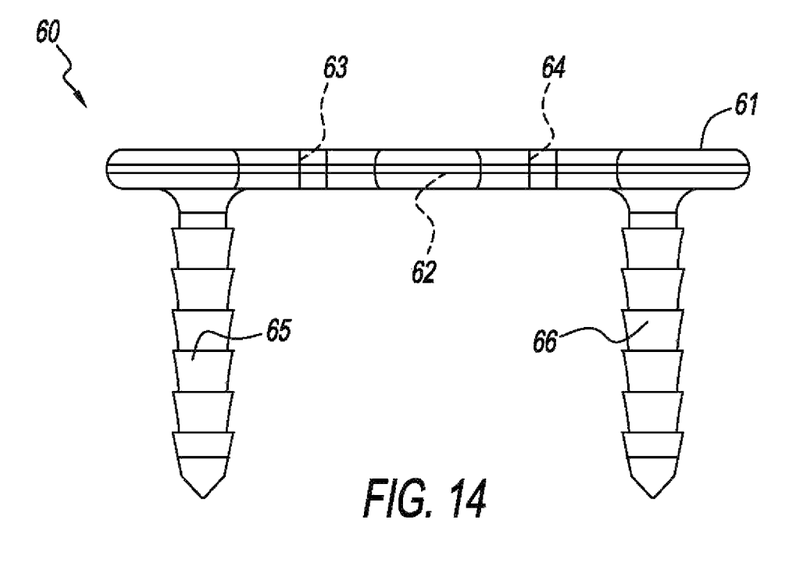
FIG. 14 is a side view of the implant expulsion prevention plate of FIG. 13.
Figure 15:
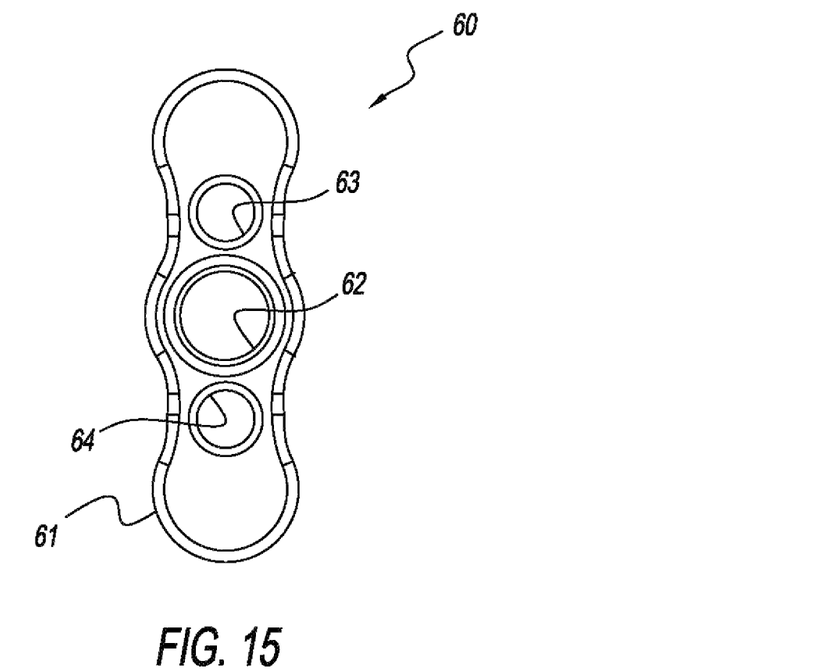
FIG. 15 is a top view of the implant expulsion prevention plate of FIG. 13.
Figure 16:
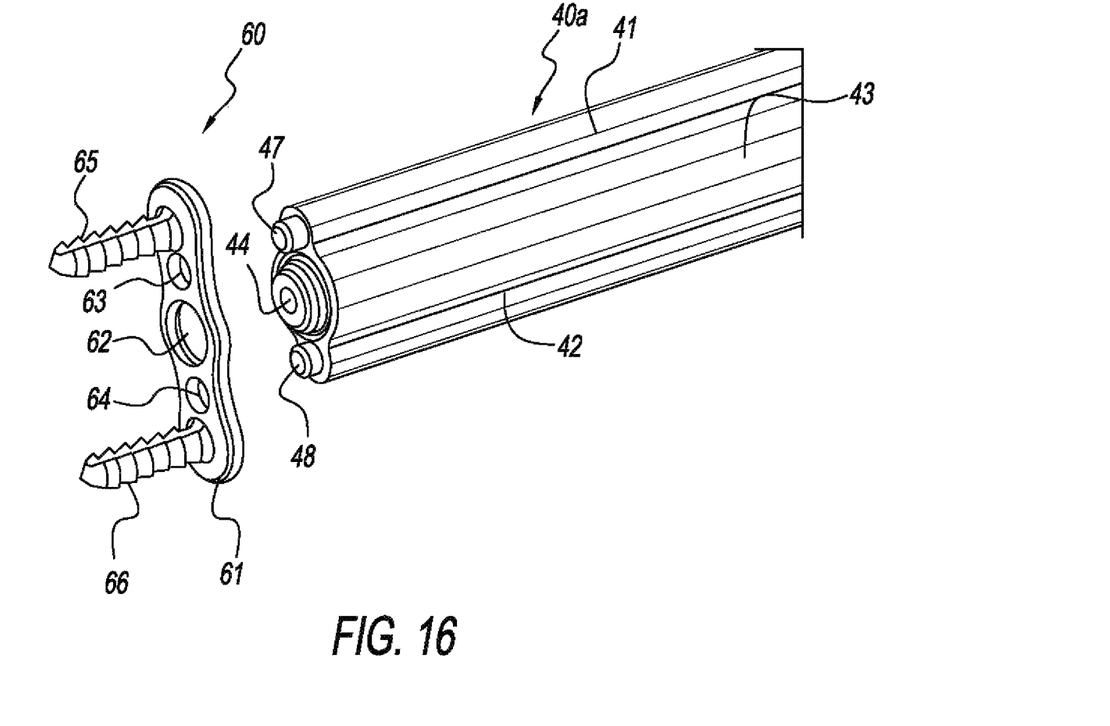
FIG. 16 is an isometric view of the end of the installation instrument for installing the implant expulsion prevention plate of FIGS. 13-15, with the plate shown exploded relative to the end of the installation instrument.
Figure 17:
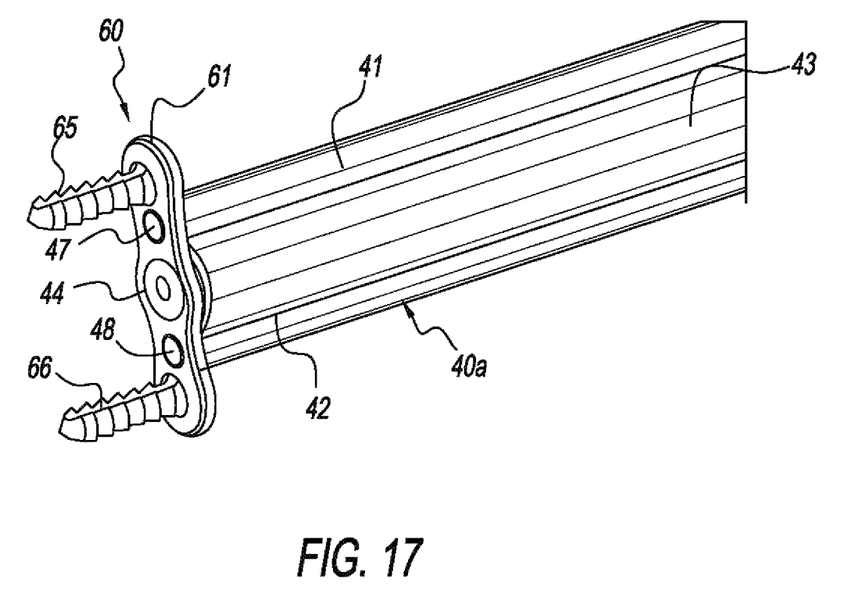
FIG. 17 is an isometric view of the end of the installation instrument of FIG. 16 with the implant expulsion prevention plate attached thereto.

Referring to FIGS. 13-15 there is shown another plate 60 for the plate construct 30. The plate 60 is fashioned from a bio-compatible material such as is known in the art, and is defined by a flat, elongated, generally planar body 61. While not shown, the body 61 may have a slight curvature for miming anatomy. The plate 60 has a plurality of bores along its length. In particular, the body 61 has a center, central, or middle threaded bore 62 of a third diameter, an upper or superior bone screw bore 63 of a fourth diameter situated laterally adjacent the central threaded bore 62 on the superior end of the body 61, and a lower or inferior bone screw bore 64 of the fourth diameter situated laterally adjacent the central threaded bore 62 on the inferior end of the body 61, the nomenclature first, second, third, and fourth being arbitrary.

The plate 60 has an integral superior connection barb ("superior barb") 65 at its superior end and an integral inferior connection barb ("inferior barb") 66 at is inferior end. The integral superior barb 65 extends from a lower superior surface of the plate 61 and is disposed laterally adjacent the superior bone screw bore 63 opposite the central threaded bore 62. The integral inferior barb 66 extends from a lower inferior surface of the plate 61 and is disposed laterally adjacent the inferior bone screw bore 64 opposite the central threaded bore 62.

Figure 18:
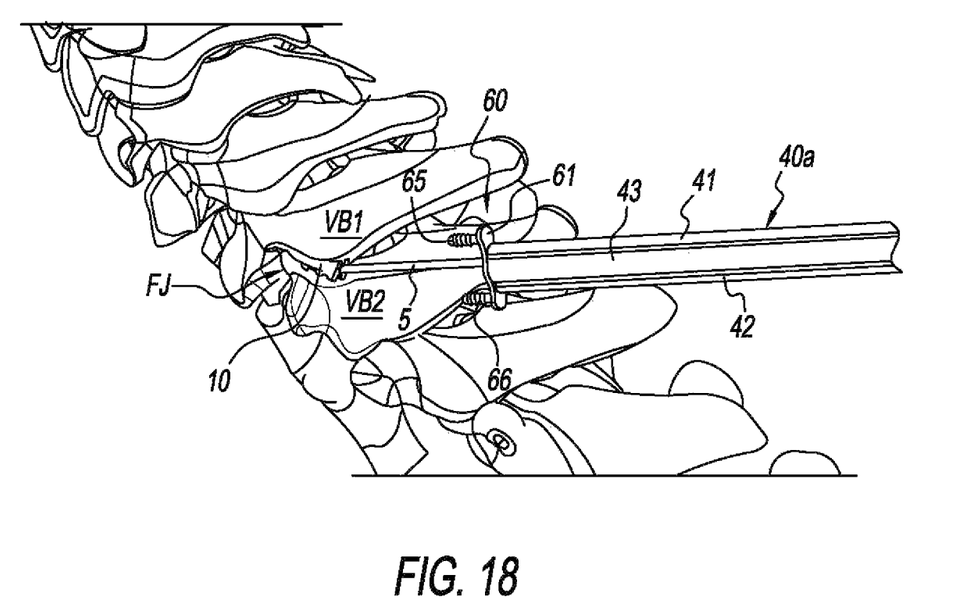
FIG. 18 is a posterior view of a portion of the spine with a wedge (implant) installed in a facet joint between a superior vertebra and an inferior vertebra, with the installation instrument and the connected plate of FIG. 17 being guided down the k-wire.
Figure 19:
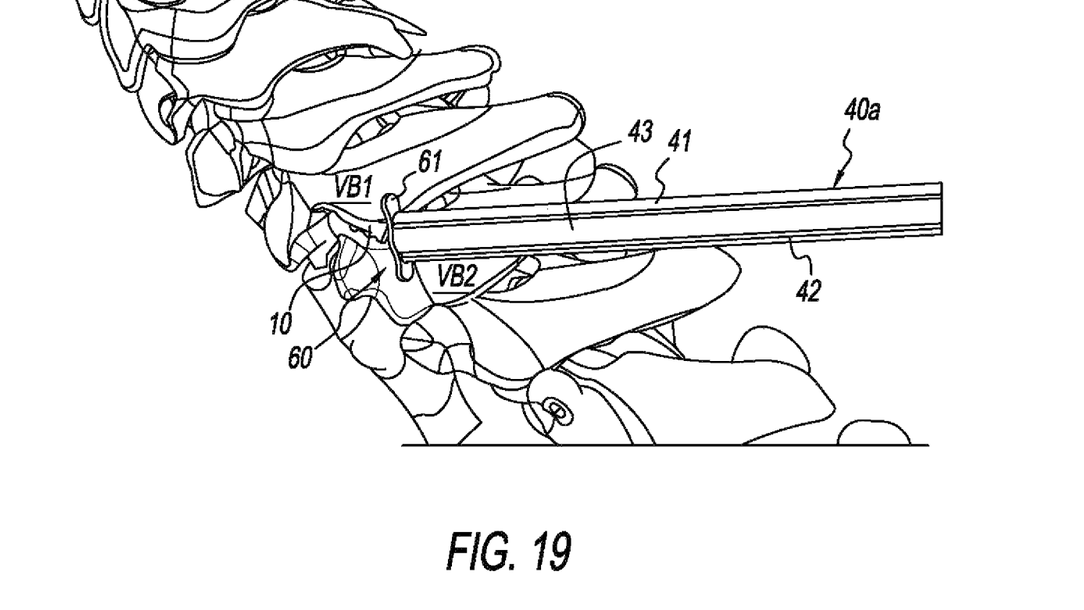
FIG. 19 is the posterior view of the portion of the spine of FIG. 18 with the installation instrument/implant expulsion plate in place.
Figure 20:
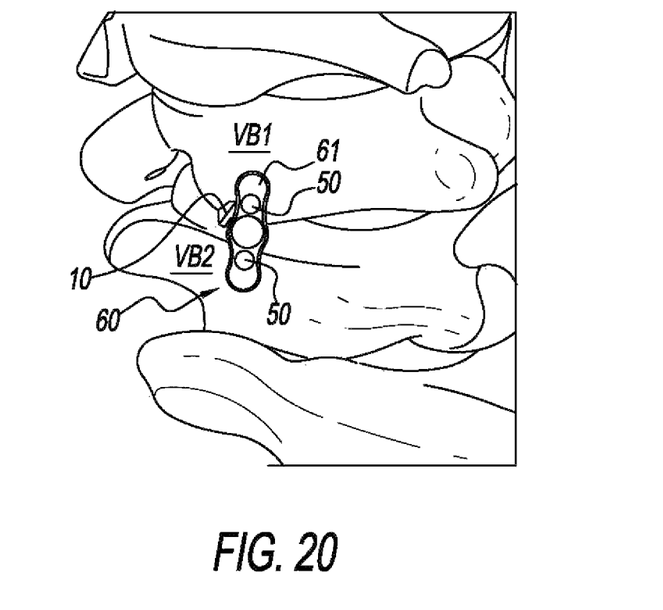
FIG. 20 is a lateral view of the plate of FIG. 19 fastened to the superior and inferior vertebrae.

Installation of the plate 60 is almost identical to the installation of the plate 20, but in any case is illustrated as herein described. Reference is made to FIGS. 16-20. Installation uses a modification of the installer, designated 40a that is made from a typical, bio-compatible surgical instrument material. The installer 40a has a center or central tube, cannula, cylinder, channel or the like 43, an upper or superior tube, cannula, cylinder, channel or the like 41 at a superior side of the central cannula 43, and a lower or inferior tube, cannula, cylinder, channel or the like 42 at an inferior side of the central cannula 43. A threaded plug 44 with a bore therethrough is shown at the end of the central cannula 43, the threaded plug 44 may be permanent to the instrument or may be a separate accoutrement tool to the construct that is received in the central cannula 43 and passed through as necessary. The end of the superior cannula 41 has a tang or nub 47 that is sized to receive the superior bone screw bore 63 of the plate 60 while the end of the inferior cannula 42 has a tang or nub 48 that is sized to receive the inferior bone screw bore 64 of the plate 60. The plate 60 is also received onto the installer 40a by threading the threaded central bore 62 of the plate 60 onto the threaded hub 44 of the installer 40a. At this point, the installer 40a is ready to allow placement of the plate 60 onto the vertebrae VB1, VB2 and over the implant 10. As shown in FIG. 18, the installer and plate are received by the k-wire 5. Particularly, the k-wire is received into bore of the threaded hub 44 and into the central cannula 43. As shown in FIG. 19, the plate 60 is guided by the installer 40a into position by the k-wire 5. The barbs 65, 66 attach the plate 60 to the vertebrae VB1, VB2 as illustrated in FIG. 20. Bone screws 50 may be additionally used in the bores 63, 64 if desired via the screw driver/installer 55 and a driving end 56 via the superior and inferior cannulas 41, 42.

The present invention has advantages over the prior art. The following is a non-exhaustive listing of the advantages. The plate is attached to a guide/installer and/or tools/accoutrements that utilizes a threaded shaft which is dual-cannulated. The plate and installer are then inserted over the K-Wire that is attached to the wedge. The installer/plate construct is placed down the k-wire and inserted posterior to the facet implant. Once the plate is in place, screws are inserted through the cannula of the guide and into a screw pocket. Both versions of the plate (screws or pre-attached barbs) are loaded in the same fashion. The two tangs of the installer prevent any rotation of the plate during insertion for the plate with the pre-installed barbs. Barbs and screws are placed superior and inferior to the facet joint implant. The present plate may use both one or more barbs and one or more screws.

It should be appreciated that more than one facet implant/wedge (implant expulsion prevention) plate of either or both forms may be used. The plates may also be stacked to provide multi-level plates/plating. Stackable plate options include, but are not limited to, single and multi-screw/barb plates per level—i.e. one barb/screw per plate or one barb/screw per level.

Moreover, the present plate of both forms may optionally include break off tabs.

Moreover, a single plate of both forms (e.g. screw or barb form) may be fashioned as a singular multi-level plate.

Furthermore, the present facet wedge plate may be integrated with facet graft for an all-in-one design.

Other variations are contemplated.

It should be appreciated that dimensions of the components, structures, and/or features of the present constructs may be altered as desired within the scope of the present disclosure.

What is claimed is:

1. A spine implant for preventing expulsion of a spinal facet joint implant from a spinal facet joint between a superior vertebra and an adjacent inferior vertebra, the spine implant comprising:

a one-piece elongate plate having a longitudinal axis, a generally planar upper surface, a generally planar lower surface, a central internally threaded bore of a first diameter, a first superior bore of a second diameter that is smaller than the first diameter and laterally adjacent the central internally threaded bore, a first superior bore countersink situated in the generally planar upper surface and surrounding the first superior bore, the first superior bore countersink extending from the generally planar upper surface of the one-piece elongate plate and into the first superior bore, a second superior bore of the second diameter and laterally adjacent the first superior bore opposite the central internally threaded bore, a second superior bore countersink situated in the generally planar upper surface of the one-piece elongate plate and surrounding the second superior bore, the second superior bore countersink extending from the generally planar upper surface of the one-piece elongate plate and into the second superior bore, a first inferior bore of the second diameter and laterally adjacent the central internally threaded bore on a side opposite to the first superior bore, a first inferior bore countersink situated in the generally planar upper surface of the one-piece elongate plate and surrounding the first inferior bore, the first inferior bore countersink extending from the generally planar upper surface of the one-piece elongate plate and into the first inferior bore, a second inferior bore of the second diameter and laterally adjacent the first inferior bore opposite the central internally threaded bore, a second inferior bore countersink situated in the generally planar upper surface of the one-piece elongate plate and surrounding the second inferior bore, the second inferior bore countersink extending from the generally planar upper surface of the one-piece elongate plate and into the second inferior bore;

a first bone fastener shaped for reception and capture in the first superior bore and securement to vertebral bone of a superior vertebra;

a second bone fastener shaped for reception and capture in the second superior bore and securement to vertebral bone of the superior vertebra;

a third bone fastener shaped for reception and capture in the first inferior bore and securement to vertebral bone of an inferior vertebra; and a fourth bone fastener shaped for reception and capture in the second inferior bore and securement to vertebral bone of the inferior vertebra;

the one-piece elongate plate sized to cover a spinal facet implant installed in a facet joint of the superior vertebra and the inferior vertebra and be attached to vertebral bone of the superior vertebra and vertebral bone of the inferior vertebra, and be releasably connectable to an externally threaded boss of an installation tool via the central internally threaded bore of the one-piece elongate plate, the one-piece elongate plate and attached installation tool adapted to be guided to the spinal facet implant via a previously installed k-wire.

2. The spine implant of claim 1, wherein the first, second, third, and fourth bone fasteners each comprise a bone screw.

3. The spine implant of claim 2, wherein the second diameter of the first superior bore, the second superior bore, the first inferior bore, and the second inferior bore is sized to allow a threaded shank of the bone screw to extend through the first superior bore, the second superior bore, the first inferior bore, and the second inferior bore, while the first superior bore countersink, the second superior bore countersink, the first inferior bore countersink, and the second inferior bore countersink, retain a head of the bone screw with a top of the head of the bone screw even with the upper surface of the one-piece elongate plate.

4. The spine implant of claim 1, wherein the first, second, third, and fourth bone fasteners each comprise a bone barb.

5. The spine implant of claim 4, wherein the second diameter of the first superior bore, the second superior bore, the first inferior bore, and the second inferior bore is sized to allow a barbed shank of the bone barb to extend through the first superior bore, the second superior bore, the first inferior bore, and the second inferior bore, while the first superior bore countersink, the second superior bore countersink, the first inferior bore countersink, and the second inferior bore countersink, retain a head of the bone barb with a top of the head of the bone barb even with the upper surface of the one-piece elongate plate.

6. The spine implant of claim 1, wherein the one-piece elongate plate comprises a one-piece longitudinally elongate plate.

7. The spine implant of claim 1, wherein the central internally threaded bore, the first superior bore, the second superior bore, the first inferior bore, and the second inferior bore are laterally aligned with one another along the longitudinal axis of the one-piece plate.

8. A spine implant kit for aiding in expulsion prevention of a previously installed spinal facet joint implant from a spinal facet joint between a superior vertebra and an adjacent inferior vertebra, the implant kit comprising:

a plurality of bone fasteners;

a spine implant consisting of a one-piece elongate plate having a longitudinal axis, a generally planar upper surface, a generally planar lower surface, a central internally threaded bore of a first diameter, a first superior bore of a second diameter that is smaller than the first diameter and laterally adjacent the central internally threaded bore, a first superior bore countersink situated in the generally planar upper surface of the one-piece elongate plate and surrounding the first superior bore, the first superior bore countersink extending from the generally planar upper surface of the one-piece elongate plate and into the first superior bore, a second superior bore of the second diameter and laterally adjacent the first superior bore opposite the central internally threaded bore, a second superior bore countersink situated in the generally planar upper surface of the one-piece elongate plate and surrounding the second superior bore, the second superior bore countersink extending from the generally planar upper surface of the one-piece elongate plate and into the second superior bore, a first inferior bore of the second diameter and laterally adjacent the central internally threaded bore on a side opposite to the first superior bore, a first inferior bore countersink situated in the generally planar upper surface of the one-piece elongate plate and surrounding the first inferior bore, the first inferior bore countersink extending from the generally planar upper surface of the one-piece elongate plate and into the first inferior bore, a second inferior bore of the second diameter and laterally adjacent the first inferior bore opposite the central internally threaded bore, a second inferior bore countersink situated in the generally planar upper surface of the one-piece elongate plate and surrounding the second inferior bore, the second inferior bore countersink extending from the generally planar upper surface of the one-piece elongate plate and into the second inferior bore; and an installation instrument for attaching the spine implant to a superior vertebra and an adjacent inferior vertebra with the plurality of bone fasteners, the installation instrument adapted to be guided to the previously installed spinal facet implant via a previously installed k-wire;

the one-piece elongate plate sized to cover the previously installed spinal facet joint implant in a facet joint of the superior vertebra and the inferior vertebra, and be releasably connectable to an externally threaded boss of the installation tool via the central internally threaded bore of the one-piece elongate plate, the one-piece elongate plate and attached installation tool adapted to be guided to the spinal facet implant via the previously installed k-wire.

9. The spine implant kit of claim 8, wherein the plurality of bone fasteners each comprise a bone screw.

10. The spine implant kit of claim 9, wherein the second diameter of the first superior bore, the second superior bore, the first inferior bore, and the second inferior bore is sized to allow a threaded shank of the bone screw to extend through the first superior bore, the second superior bore, the first inferior bore, and the second inferior bore, while the first superior bore countersink, the second superior bore countersink, the first inferior bore countersink, and the second inferior bore countersink, retain a head of the bone screw with a top of the head of the bone screw even with the upper surface of the one-piece elongate plate.

11. The spine implant kit of claim 8, wherein the plurality of bone fasteners each comprise a bone barb.

12. The spine implant kit of claim 11, wherein the second diameter of the first superior bore, the second superior bore, the first inferior bore, and the second inferior bore is sized to allow a barbed shank of the bone barb to extend through the first superior bore, the second superior bore, the first inferior bore, and the second inferior bore, while the first superior bore countersink, the second superior bore countersink, the first inferior bore countersink, and the second inferior bore countersink, retain a head of the bone barb with a top of the head of the bone barb even with the upper surface of the one-piece elongate plate.

13. The spine implant kit of claim 8, wherein the one-piece elongate plate comprises a one-piece longitudinally elongate plate.

14. The spine implant kit of claim 8, wherein the central internally threaded bore, the first superior bore, the second superior bore, the first inferior bore, and the second inferior bore are laterally aligned with one another along the longitudinal axis of the one-piece elongate plate.

\* \* \* \* \*